(12) United States Patent
Couillard et al.

(10) Patent No.: US 6,227,541 B1
(45) Date of Patent: May 8, 2001

(54) MULTIPLE CONVEYOR ASSEMBLY AND METHOD FOR ROTATING AND PLACING A STRIP OF MATERIAL ON A SUBSTRATE

(75) Inventors: Jack L. Couillard, Menasha; Brian K. Rhodes, Larsen, both of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/346,247

(22) Filed: Jul. 1, 1999

(51) Int. Cl.[7] .................................................. B65H 29/54
(52) U.S. Cl. ..................... 271/307; 198/408; 198/689.1; 225/184; 225/185
(58) Field of Search ................................. 198/408, 689.1; 271/225, 69, 306, 307, 310, 311, 185; 225/184, 185

(56) References Cited

U.S. PATENT DOCUMENTS

| 4,124,429 | 11/1978 | Crankshaw . | | |
|---|---|---|---|---|
| 5,048,818 | 9/1991 | Nemeskal . | | |
| 5,104,116 | 4/1992 | Pohjola . | | |
| 5,112,041 | * 5/1992 | Honegger | ............. | 271/286 |
| 5,224,405 | 7/1993 | Pohjola . | | |
| 5,333,851 | * 8/1994 | Kulpa | ............. | 271/225 |
| 5,571,354 | 11/1996 | Miyamoto . | | |

FOREIGN PATENT DOCUMENTS

| 0 450 650 | 10/1991 | (EP) . |
|---|---|---|
| 243500 | * 8/1966 | (SU) . |
| 99/24334 | 5/1999 | (WO) . |

* cited by examiner

Primary Examiner—Donald P. Walsh
Assistant Examiner—Jonathan R. Miller
(74) Attorney, Agent, or Firm—Pauley Petersen Kinne & Fejer

(57) ABSTRACT

A conveyor assembly and method for rotating a strip of material via one or more transfer elements angularly disposed relative to the initial orientation of the strip of material and placing the rotated strip of material toward a continuously moving surface.

32 Claims, 5 Drawing Sheets

MULTIPLE CONVEYOR ASSEMBLY AND METHOD FOR ROTATING AND PLACING A STRIP OF MATERIAL ON A SUBSTRATE

FIELD OF THE INVENTION

This invention relates generally to rotating strips of material and, more specifically, the invention relates to rotating strips of material and then placing the rotated strips in surface contact with a continuously moving surface.

BACKGROUND OF THE INVENTION

Various apparatus are available that receive strips of cut material and then manipulate the material strips such as by either or both rotating or pivoting the strips relative to their initial direction of movement and then placing such material strips on or near a continuously moving surface. In placing the strips of material relative to the moving surface, such apparatus generally begin the placement by initially contacting the leading edge of the strip with the moving surface and then progressively laying or rolling the strip upon the surface with the trailing edge of the strip being the last to be laid upon the moving surface.

A problem that exits with these apparatus is that rotation of the transferring element, upon which the strip is carried, can cause the transferring element to bite or dig into the moving surface, thereby undesirably cutting or otherwise damaging the moving surface. For example, as the transferring element releases the leading edge of the material strip and then begins to pivot or rotate upwardly away from the moving surface, the trailing edge of the transferring element pivots or rotates against and into the moving surface. This can either or both damage the moving surface and disrupt the proper positioning or registration of the strip with the moving surface, and is particularly undesirable when the moving surface is a woven or nonwoven material.

This problem is particularly acute when the strip being laid upon the moving surface is of a generally elongate or rectangular shape having its longest axis parallel to the direction of movement of the moving surface.

Another frequently occurring problem in such processing relates to the proper releasing of the strip of material from the transferring element to the moving surface. Generally, such strips of material are held on their respective transferring elements via a vacuum effect created or transmitted through perforations or holes in the outer surface of the transferring element. Unfortunately, these apparatus may not extinguish or otherwise release the vacuum against the strip of material as the strip of material is progressively transferred leading edge to trailing edge on the moving surface. For example, if the vacuum is not progressively extinguished as the strip is progressively laid from the transferring element onto the surface, portions of the strip element can continue to be held by vacuum against the transferring element resulting in an undesirable pleat or fold in the strip material, skewed alignment of the strip material with the moving surface, and the like.

In view of these and other perceived shortcomings in prior existing apparatus and processing relating to the receiving and rotating strips of material and then placing the rotated strips relative to a continuously moving surface, a new applicator apparatus and application process have been developed and are the subject of Pohjola, U.S. Pat. No. 5,104,116, issued Apr. 14, 1992, and Pohjola, U.S. Pat. No. 5,224,405, issued Jul. 06, 1993, the disclosures of each of which is incorporated herein by reference in its entirety. In accordance therewith, a strip of material is received and rotated toward a continuously moving surface, and then orientated so that the surface thereof is placed generally flat with the continuously moving surface via one or more puck rotating means. In accordance with certain preferred embodiments thereof, the apparatus additionally includes a surface-leveling means for positioning the puck surface in an appropriate spaced-apart relationship with the moving surface. To that end, these patents disclose puck assemblies which in addition to rotating, pivot such that the puck surface is placed flat against or with the moving surface, as desired, and such as may employ open cams.

While such apparatus and associated processing have represented a significant advancement in the art and have generally been successful in overcoming, reducing or minimizing at least some of the problems or shortcomings of earlier apparatus and processing, such apparatus and processing may at least at times be subject to certain limitations. For example, the employment of features such as puck members which both pivot and rotate such as to receive, rotate and deposit such material strips may result in the undesirable introduction of oscillating or reciprocating motion into the apparatus and processing.

As will be appreciated, such motion may interfere with desired operation. In particular, such oscillating or reciprocating motion may complicate or prevent either or both the proper positioning and placement of the strip of material on an associated moving surface. Also, the requirement to oscillate or reciprocate mass introduces inertia and can act as a speed limiter because force increases with speed. Reciprocating or oscillating motions can limit process speed because inertial forces in the mechanism can exceed the capability of engineering materials and methods. In addition, reciprocating or oscillating mechanisms tend to require frequent and costly maintenance due to wear caused by high inertial forces.

Thus, there remains a need and a demand for further improvements with respect to apparatus and processing for receiving and rotating strips of material and then placing the rotated strips in surface contact with a continuously moving surface.

SUMMARY OF THE INVENTION

A general object of the invention is to provide an improved assembly and method for rotating a strip of material and placing the rotated strip of material in surface contact with a moving surface.

The general object of the invention can be attained, at least in part, through an assembly which includes a conveyor and an associated transfer subassembly. In accordance with one preferred embodiment of the invention, the conveyor includes at least a first conveyance surface on which a strip of material is conveyed in a first direction. The transfer subassembly includes at least a first transfer element angularly disposed at a first selected degree of angular rotation relative to the first direction. The transfer subassembly is effective to secure the strip of material from the first conveyance surface and deposit the strip of material on a first adjacent moving surface moving at the first selected degree of angular rotation.

The prior art generally fails to provide as effective and as efficient as desired apparatus and method for the receiving and rotating strips of material and then placing the rotated strips in surface contact with a continuously moving surface. More particularly, the prior art generally fails to provide such apparatus and method that minimize or avoid the undesirable introduction of oscillating or reciprocating motion to as great an extent as may be desired.

The invention, in accordance with an alternative embodiment of the invention, further comprehends an assembly which includes a conveyor and an associated transfer subassembly. In such an assembly, the conveyor includes at least a first conveyance surface on which a strip of material is conveyed in a first direction. The transfer subassembly includes at least first and second vacuum transfer rolls.

The first vacuum transfer roll is angularly disposed at a first selected degree of angular rotation relative to the first direction. The first vacuum transfer roll is effective to secure the strip of material from the first conveyance surface and deposit the strip of material on a first adjacent moving surface having a conveyance direction orientated at the first selected degree of angular rotation.

The second vacuum transfer roll is angularly disposed at a second selected degree of angular rotation relative to the first selected degree of angular rotation. The second vacuum transfer roll is effective to secure the strip of material from the first adjacent moving surface and deposit the strip of material on a second adjacent moving surface having a conveyance direction orientated at the second selected degree of angular rotation.

In the assembly, the first conveyance surface and the first vacuum transfer roll have conveyance velocities with similar magnitude components in the first direction. In addition, the first adjacent moving surface has a conveyance velocity that matches the surface velocity of the first vacuum transfer roll. Also, the first adjacent moving surface and the second vacuum transfer roll have conveyance velocities with similar magnitude components in the conveyance direction of the first adjacent moving surface. Finally, the second vacuum transfer roll has a conveyance velocity that matches the second adjacent moving surface.

The invention still further comprehends methods for rotating a strip of material and placing the rotated strip of material in surface contact with a moving surface. In accordance with one such preferred method, at least one strip of material having a first axis in a first angular orientation on a first continuously moving conveyance surface is initially provided. The at least one strip of material is subsequently secured from the first conveyance surface onto a first transfer element angularly disposed at a first selected degree of angular rotation relative to the first angular orientation. The at least one strip of material is then transferred from the first transfer element onto a first adjacent moving surface.

As used herein, references to conveyance velocities, angular rotations and the like parameters or characteristics as having or being of "similar magnitude" are to be understood as generally referring to the values of such respective parameter or characteristic as being within no more than a few percent of each other, typically within less than about 5% of each other and, more particularly, within no more than about 1–3% of each other.

Other objects and advantages will be apparent to those skilled in the art from the following detailed description taken in conjunction with the appended claims and drawings.

DETAILED DESCRIPTION OF THE PRESENTLY PREFERRED EMBODIMENTS

The present invention, as is described in more detail below, provides an improved assembly and method for rotating a strip of material and placing the rotated strip of material in surface contact with a moving surface. In particular, in accordance with one preferred embodiment, the invention reduces or eliminates either or both reciprocating and oscillating motion.

Figure 1:
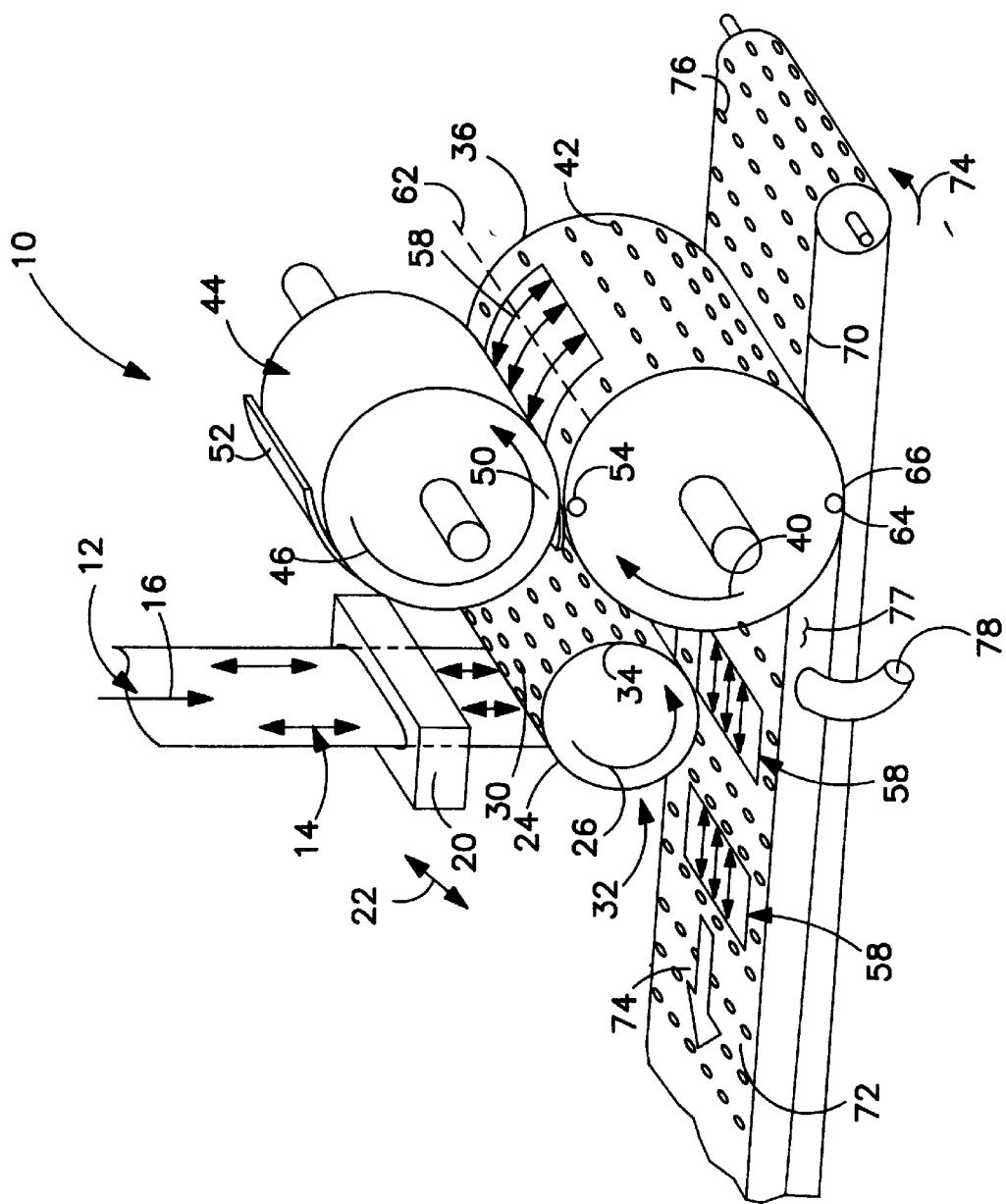
FIG. 1 is a simplified fragmentary perspective schematic of an assembly for forming strips of material from a continuous web for use in the practice of the invention.

Referring to FIG. 1, there is illustrated an assembly, generally designated by the reference numeral 10 and such as may be used in the formation of discrete strips of material such as may be used in the practice of the invention.

As shown, a continuous web 12 is introduced to the assembly 10 such as via a conveyor belt from any suitable web supply assembly (not shown), such as a controlled tension unwind, for example. The web 12 can be of any type of material such as a woven or nonwoven material, and can be supplied as a single web or ribbon of material, or a plurality of webs or ribbons of material. If there is a plurality of webs or ribbons of material, the materials of which the webs or ribbons are made can also be different. Example of nonwoven webs include, but are not limited to, paper and paper-like material, pressure-sensitive tape material, mechanical fastener material such as hook-and-loop material, films of thermoplastic material, spun bond or melt blown thermoplastic material, an elastomeric material, or a stretch bond laminate material. A stretch bond laminate material comprises a stretchable material that is stretched and then bonded to a gatherable material and then allowed to relax to form the laminate.

In accordance with one preferred embodiment of the invention, the continuous web 12 desirably is a stretchable spun bond laminate ("SBL"), with stretch in the direction of the arrows 14. In FIG. 1, the web 12 has an initial direction of conveyance or travel indicated by the arrow 16. In the illustrated embodiment, the direction of stretch and such direction of conveyance for the web coincide.

If desired, and as shown, the continuous web 12 may be introduced via a web steering device 20, as is generally known in the art, such as to assist in maintaining proper and desired positioning and placement of the web 12 in the cross machine direction, signified by the arrow 22. As will be appreciated, such a web steering device, if included, may be present either as a separate device or apparatus or as a part of the assembly 10, as may be desired.

The continuous web 12 is transferred to a rotatable vacuum feed roll 24 having a direction of rotation signified by the arrow 26. The vacuum feed roll 24 has a plurality of perforations 30 therein. A vacuum is created, generated or provided within the vacuum feed roll 24, such as is known in the art and such as may serve to hold the web 12 thereto. In the particularly illustrated embodiment, the vacuum feed roll 24 holds the web 12 with a controlled vacuum from about the 9 o'clock position 32 to a tangent point 34 of the vacuum feed roll 24 with an associated rotatable vacuum anvil roll 36.

At the tangent point 34, the web 12 is transferred to the rotatable vacuum anvil roll 36 which has a direction of rotation signified by the arrow 40. Similarly to the rotatable vacuum feed roll 24 described above, the rotatable vacuum anvil roll 36 has a plurality of perforations 42 therein. A vacuum created, generated or provided within the anvil roll 36, such as is known in the art, serves to hold the web 12 lightly to the anvil roll 36.

The web 12 on the anvil roll 36 is acted upon by a rotatable knife roll 44 which has a direction of rotation signified by the arrow 46. The knife roll 44 includes first and second cutting edges 50 and 52, respectively. More specifically, the first knife roll cutting edge 50 contacts a first cutting surface 54 on the anvil roll 36 or otherwise serves to cut the web into discrete strips of material 58, having a longitudinal axis 62. The second knife roll cutting edge 52 similarly contacts a second cutting surface 64 on the anvil roll 36 or otherwise serves to correspondingly cut a subsequent portion of the web into an additional discrete strip of material.

In the illustrated assembly 10, the knife roll 44 is a two-repeat roll which is geared (timed) to the anvil roll 36 to make a cut each half revolution. The anvil roll 36 is desirably sized such that it has a circumference in which is a multiple of the product repeat length and a suitable draw. In the illustrated assembly 10, the anvil roll 36 is a two-repeat roll.

The strip cutting assembly 10 described above is sometimes referred to as a slip cut assembly as, in such an assembly, the web 12 can desirably slip on the surface of the anvil roll until it is cut. In practice, the speed of rotation of the vacuum feed roll can be selected to provide the desired amount (length) for the strips of material.

Further, a vacuum feed roll having a roughened web-contacting surface can desirably be employed. As will be appreciated, a vacuum feed roll having a roughened web-contacting surface can result in increased friction between the web material and the web-contacting surface thereof such as can desirably reduce the amount of vacuum required in order to properly maintain the associated web material relative thereto. One technique for obtaining such a suitably roughened surface is via the application onto the feed roll of an appropriate plasma spray coating, such as known in the art. Other techniques for such surface roughening will be apparent to those skilled in the art and can, if desired, be used.

As will be appreciated, the broader practice of the invention is not necessarily limited by the size of the rolls or the number of cutting edges as for example, knife rolls with one or more cutting edges can be used. Further, suitable cutting devices other than knife rolls and such as known in the art can, if desired, be used.

In accordance with the invention, the size or dimensions of the material strips 58 can be selected to meet the requirements of a specific use thereof. For example, such strips of material of a longitudinal length of about 15 inches and a lateral width of about 3 inches are well suited for use in association with the manufacture and production of disposable pant-like garments for absorbing human discharge. It is to be understood, however, that the broader practice of the invention is not necessarily limited to material strips of such length and/or width or to the manufacture or production of such specific items of manufacture.

The anvil roll 36 holds first the web 12 and then, upon formation, the strips of material 58 with a controlled vacuum from the tangent point 34 to a tangent point 66 of the anvil roll 36 with a lower vacuum conveyor 70. In the illustrated preferred embodiment, the lower vacuum conveyor 70 has a conveyance speed which matches the speed of the anvil roll 36. The lower vacuum conveyor 70 includes a conveyance surface 72 on which the material strips 58 are conveyed in a direction signified by the arrows 74. In a manner similar to that described above, the conveyance surface 72 includes a plurality of perforations 76 therein such as to permit a vacuum created, generated or provided in or by the conveyor 70 to hold the material strips 58 thereto. More particularly and as shown in FIG. 1, such vacuum may be so provided by means of a vacuum chamber 77 underlying a selected portion of the conveyance surface 72 and an associated vacuum-supplying hose 78, such as is generally known in the art.

Figure 2:
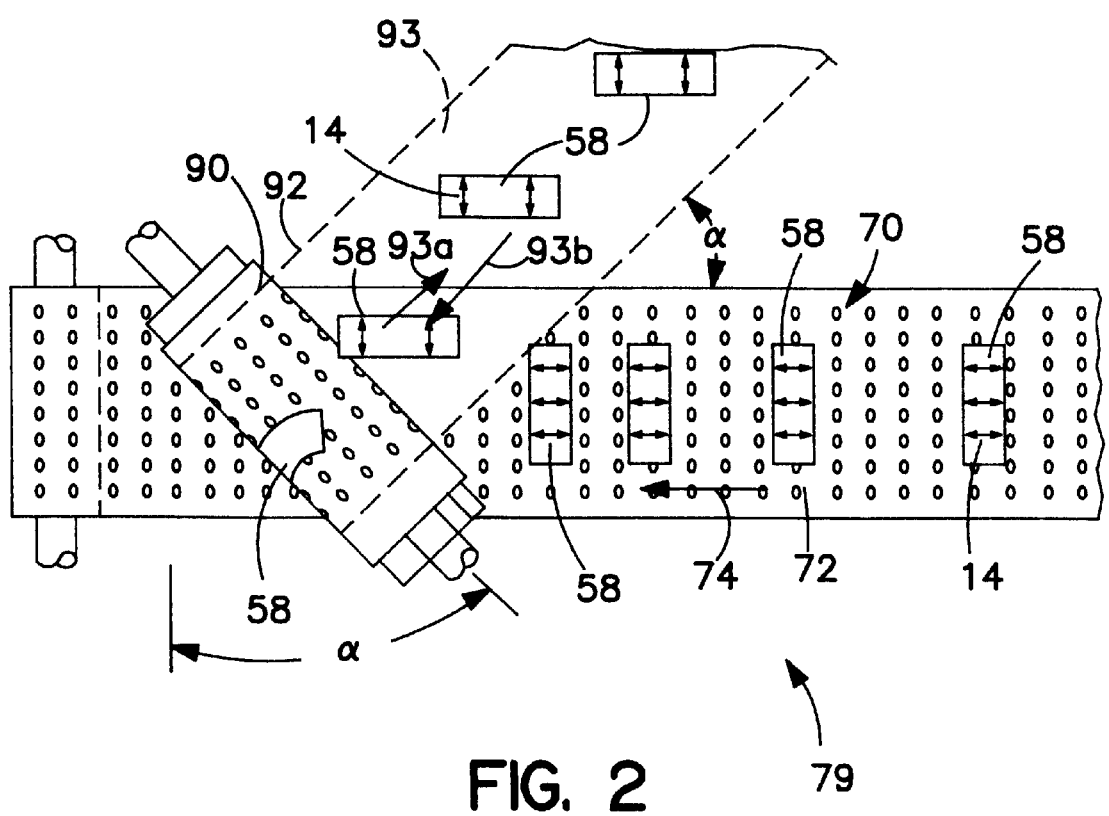
FIG. 2 is a simplified fragmentary top view schematic of a first portion of an assembly in accordance with one preferred embodiment of the invention.
Figure 3:
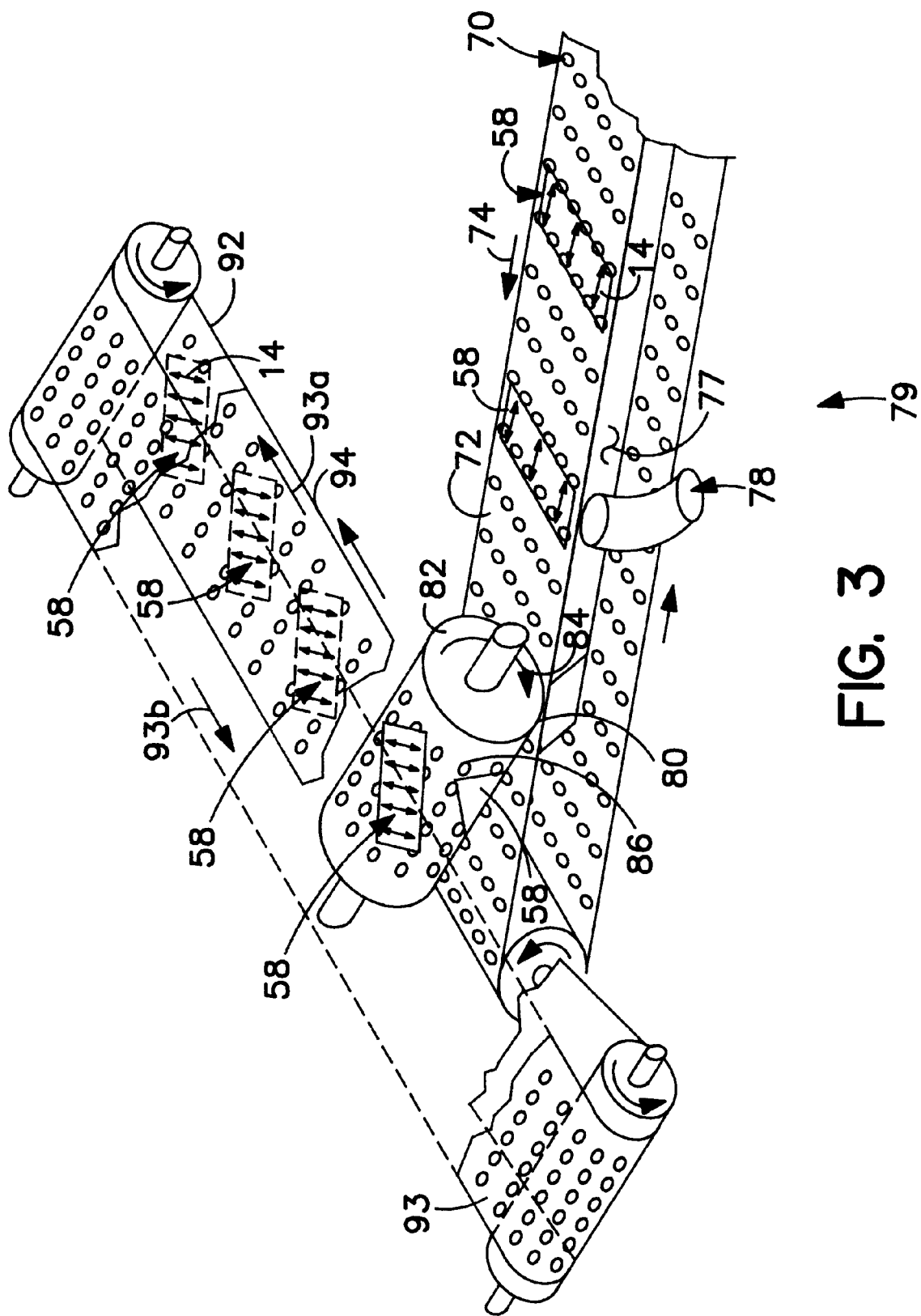
FIG. 3 is a simplified fragmentary isometric view of the first portion of the assembly generally corresponding to that shown in FIG. 2.

Turning now to FIGS. 2 and 3, a first portion, generally designated by the reference numeral 79, of an assembly in accordance with one preferred embodiment of the invention is shown in simplified form. In such first assembly portion 79, the lower vacuum conveyor 70 continues the conveyance of the strips of material 58 having a direction of stretch again signified by the arrows 14. As shown, the strips of material 58 desirably are evenly spaced on the conveyance surface 72. In particular, the vacuum of the conveyor 70 holds the strips of material 58 with a controlled vacuum, such as via the vacuum chamber 77 and associated vacuum-supplying hose 78 (shown in FIG. 3), to a tangent point 80 of the vacuum conveyor 70 with a first vacuum transfer element 82. At the tangent point 80, the strips of material 58 are individually and successively transferred onto the first vacuum transfer element 82, here in the form of a first vacuum transfer roll. The first vacuum transfer roll 82 is, as more specifically shown in FIG. 2, angularly disposed at a first selected angular rotation (α) relative to the conveyance direction signified by the arrow 74. Typically, such first selected degree of angular rotation is at least about 25 degrees. In particular embodiments, such first selected degree of angular rotation is preferably in the range of at least about 40 to about 50 degrees with the degree of angular rotation in the preferred illustrated embodiment being about 45 degrees. As will be appreciated and as may be desired, other degrees of angular rotation can be appropriately selected dependent upon the specific requirements of a particular application.

The first vacuum transfer roll 82 has a direction of rotation signified by the arrow 84 (shown in FIG. 3). In addition, the first vacuum transfer roll 82 has a velocity component in the direction of travel of the lower vacuum conveyor 70 signified by the arrow 74 that matches the belt speed of the conveyor 70. In practice, where the first vacuum transfer roll 82 is angularly disposed at an angular rotation of 45 degrees relative to the conveyance direction signified by the arrow 74, the first vacuum transfer roll 82 will have surface speed of about √2 faster than the lower vacuum conveyor 70 in order to have a matching velocity component in the direction of conveyance or travel signified by the arrow 74.

The first transfer roll 82 has a plurality of perforations 86 therein whereby a vacuum created, generated or provided within the first transfer roll 82 serves to hold successive material strips 58 thereto. The vacuum of the first vacuum transfer roll 82 is effective to hold the strips of material 58 with a controlled vacuum starting at the tangent point 80 to a tangent point 90 with a vacuum conveyor 92.

The conveyor 92 includes a conveying surface, e.g., a conveyor belt 93. To simplify illustration and facilitate comprehension, the conveyor belt 93 is shown in outline in FIG. 2 and partially in outline in FIG. 3. The conveyor belt 93 has an underside direction of conveyance signified by the arrow 93a and a upperside direction of travel signified by the arrow 93b.

At the tangent point 90, the strips of material 58 are transferred onto the vacuum conveyor 92, specifically to a vacuum belt underside 94 thereof. The vacuum conveyor 92 is orientated at the first angular rotation α (which in the specifically illustrated embodiment is 45 degrees) relative to the conveyance direction signified by the arrow 74 and includes perforations 96 whereby the strips of material 58 are held to the vacuum belt underside 94 by means of a vacuum. As will be appreciated, such vacuum can be provided by means of an adjacent vacuum chamber such as supplied by an associated vacuum-supplying hose or duct such as in a manner similar to the above-described vacuum conveyor 70. However, to simplify illustration and facilitate comprehension, such known features have not been here shown.

Figure 4:
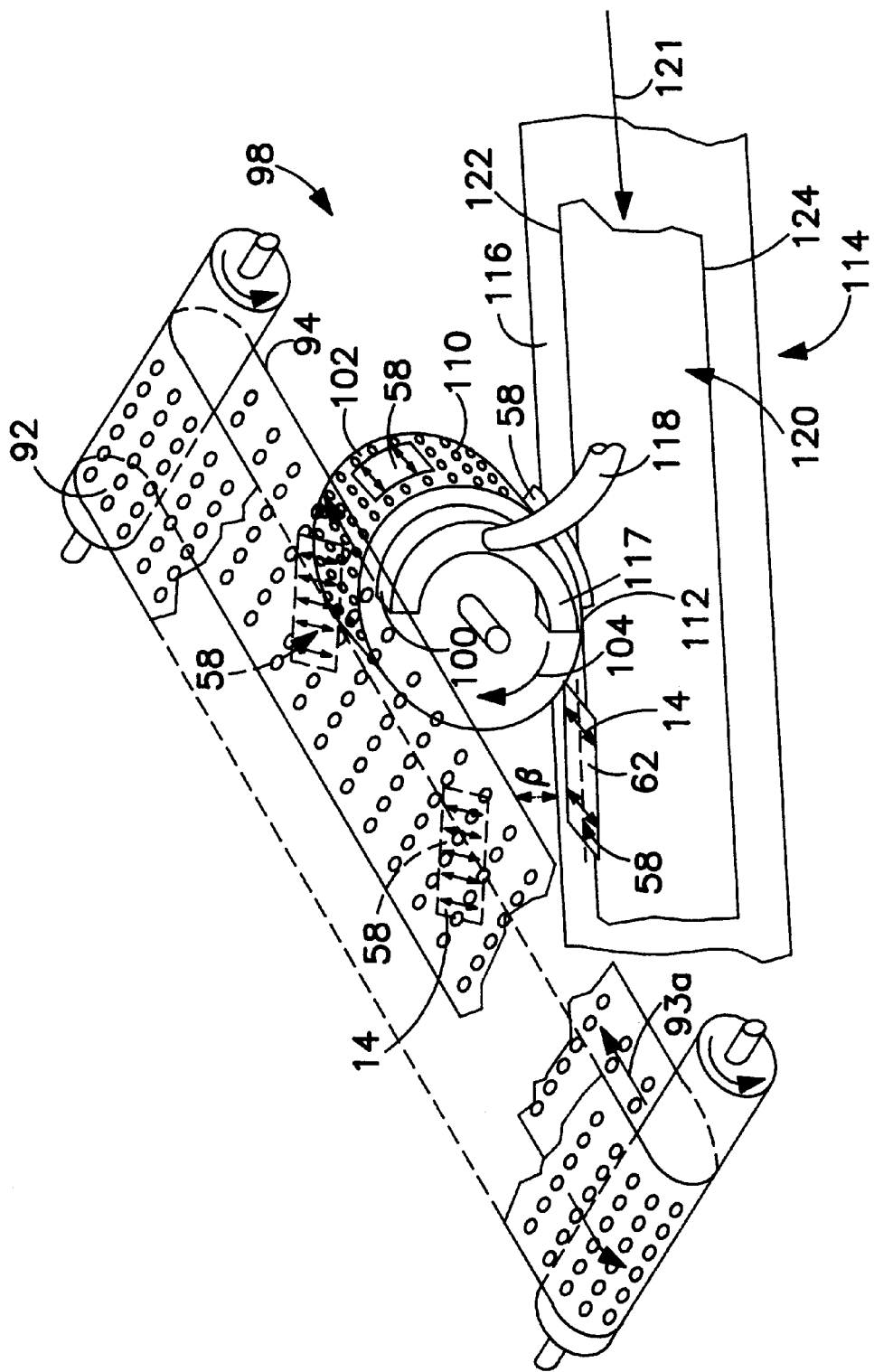
FIG. 4 is a simplified fragmentary isometric view of a second, following, portion of the assembly shown in FIGS. 2 and 3.

Turning now to FIG. 4, there is illustrated in simplified form a second following portion of the assembly in accordance with a preferred embodiment of the invention. This second portion is generally designated by the reference numeral 98. As shown, the strips of material 58 are held to the underside 94 of the conveyor 92 with a vacuum until a tangent point 100 with a second transfer element 102. At the tangent point 100, the strips of material 58 are individually and successively transferred onto the second vacuum transfer element 102, here in the form of a second vacuum transfer roll.

The second vacuum transfer roll 102 is angularly disposed at a second selected angular rotation (β) relative to the conveyor 92 conveyance direction signified by the arrow 93a. Similar to the above-described first selected angular rotation (α), the second selected angular rotation (β) typically is at least about 25 degrees. In particular embodiments, such selected second degree of angular rotation is preferably in the range of at least about 40 to about 50 degrees with the second degree of angular rotation in the preferred illustrated embodiment being about 45 degrees. As will be appreciated, in the illustrated embodiment the first and second degrees of angular rotation total or sums to 90 degrees such that the invention results in the desirable right angle rotation of the strips of material from their original orientation. It is to be understood that other degrees of angular rotation can be appropriately selected dependent upon the specific requirements of a particular application.

The second vacuum transfer roll 102 has a direction of rotation signified by the arrow 104. In addition, the second vacuum transfer roll 102 has a velocity component in the conveyor 92 direction of travel signified by the arrow 93a that matches the belt speed of the conveyor 92. Thus, similarly as described above relative to the first vacuum transfer roll 82, here where the second vacuum transfer roll 102 is angularly disposed at an angular rotation of 45 degrees relative to the conveyance direction signified by the arrow 93a, the second vacuum transfer roll 102 will have surface speed of about √2 faster than the belt speed of the conveyor 92 in order to have a matching velocity component in the direction of conveyance or travel signified by the arrow 93a.

The second transfer roll 102 has a plurality of perforations 110 therein whereby a vacuum created, generated or provided within the second transfer roll 102 serves to hold successive material strips 58 thereto. The vacuum of the second vacuum transfer roll 102 is effective to hold the strips of material 58 with a controlled vacuum starting at the tangent point 100 to a tangent point 112 with a product assembly or aligning conveyor 114, having a conveyor belt 116. To that end and as shown in FIG. 4, such vacuum may be so provided by means of a vacuum shoe 117 underlying a selected portion of the surface of second transfer roll 102 and an associated vacuum-supplying hose 118, as is generally known in the art. It will be appreciated that vacuum supplying means may similarly be utilized in the above-described vacuum rolls but have not been shown to simplify illustration and facilitate comprehension.

At the tangent point 112, the strips of material 58 are transferred onto the product assembly conveyor 114, specifically onto a belt 116 thereof and which belt 116 conveys a continuous substrate 120. The substrate 120 on the belt 116 has a general direction of conveyance or travel signified by the arrow 121. Further, the substrate 120 can be delivered thereto from any conventional type of supply assembly such as known in the art. In practice, the substrate 120 can be any type of woven or nonwoven material. The material strips applied, e.g., rolled onto, the substrate 120 can be held, fastened, joined or the like thereto by various techniques or means such as known in the art. For example, such material strips can be glued or bonded to the substrate.

In practice, a continuous substrate of a form commonly referred to as a "sausage" is used. Such a continuous substrate is generally composed of various layers of materials such as desired and included in the particular product being processed. For example, for a disposable pant-like garment for absorbing human discharge herein described, such a continuous substrate or sausage is generally an assembly composed of one or more layers of material. While such a garment can be variously constructed, in practice such a garment will typically include one or more liquid-pervious liners, absorbent inserts, and a liquid impervious outer cover such as composed of a cloth-like material. The continuous substrate 120 additionally may generally include flaps, waist band elastic, leg elastics, etc. or the like such as may serve to facilitate the placement and attachment of the final product onto an appropriate individual. In practice, the continuous substrate will have a repeat length which will be dependent on the grade or size of the specific garment product being manufactured. For example, a children's training pant garment will typically be formed using a continuous web having a repeat length of about 16 to about 32 inches with the specific repeat length again being dependent on the grade or size of the training paint garment being formed.

It will be understood, however, that the broader practice of the invention is not limited by the specific construction, shape, form or size of the substrate or the product being processed. For example, if desired, the invention can be practiced in conjunction with a substrate composed of a single material. Further, although the web 12 and the substrate 120 have been described as continuous materials, the present invention also contemplates that the substrate 120 can be a series of discrete material sheets and that the web 12 can be supplied to the assembly of the invention as discrete strips or ribbons of material.

The present invention is utilized in this embodiment to rotate the strips of material 90 degrees relative to the initial direction of movement, as indicated by the arrow 74 (shown in FIGS. 1–3), and subsequently deposited on an adjacent moving surface. In particular, the rotated strips of material are deposited along a first longitudinal side 122 of the substrate 120 such that the longitudinal axis 62 of the strips of material are generally parallel to the substrate 120 direction of movement 121.

Figure 5:
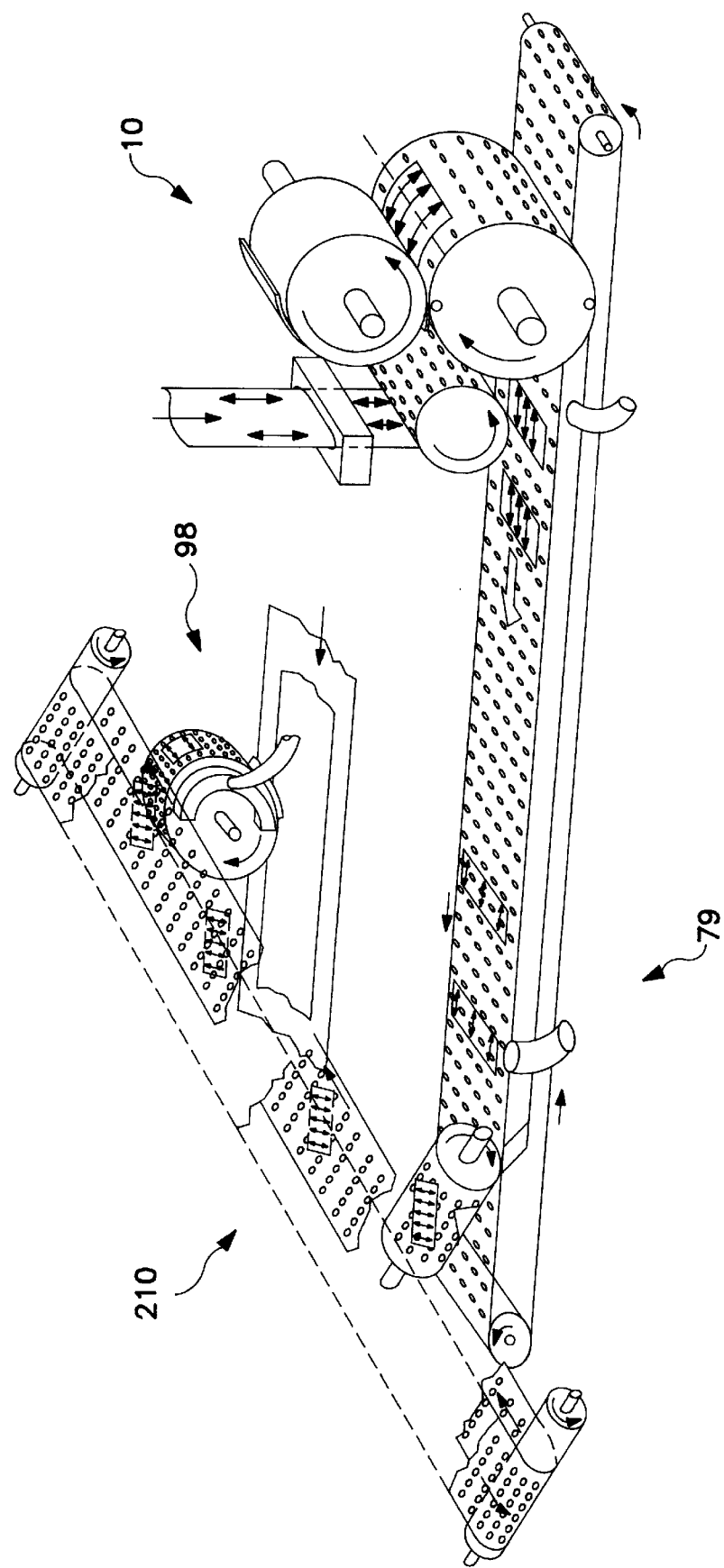
FIG. 5 is a perspective schematic of an assembly including the subassembly for forming strips of material from a continuous web, shown in FIG. 1 and the first and second assembly portions shown in FIGS. 2 and 4, respectively.

FIG. 5 illustrates the assembly, here designated by the reference numeral 210, formed by including the assembly 10 and assembly first and second portions, 79 and 98, respectively, described above.

While the invention has been described above relative to the depositing and securing of strips of material along a first side 122 of a product sausage, it will be appreciated that the invention can correspondingly be practiced to alternatively or in addition deposit and secure strips of material along a second, opposed side 124 thereof.

The present invention may also be adapted to place a plurality of strips of material with a multiple number of substrates in a manner similar to that just described.

In view of the above, it will be appreciated that the present invention provides apparatus and methods for rotating a strip of material and placing the rotated strip of material in surface contact with a moving surface of either or both generally improved effectiveness and efficiency. More particularly, the present invention generally provides such apparatus and methods that minimize or avoid the undesirable introduction of oscillating or reciprocating motion to a greater extent than possible with prior assemblies and processing. In accordance with one preferred embodiment, the invention advantageously eliminates reciprocating, oscillating motion and replaces it with a continuous process.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. An assembly comprising:
   a conveyor including at least a first conveyance surface on which a strip of material is conveyed in a first direction and
   a transfer subassembly including at least a first transfer element angularly disposed at a first selected degree of angular rotation relative to the first direction and effective to secure the strip of material from the first conveyance surface and deposit the strip of material on a first adjacent moving surface moving at the first selected degree of angular rotation, the transfer subassembly also including a second transfer element angularly disposed at a second selected degree of angular rotation relative to the first selected degree of angular rotation and effective to secure the strip of material from the first adjacent moving surface and deposit the strip of material on a second adjacent moving surface moving at the second selected degree of angular rotation and wherein at least one of the first and second transfer elements comprises a vacuum roll.

2. The assembly of claim 1 wherein the first conveyance surface and the first transfer element have conveyance velocities with same magnitude components in the first direction.

3. The assembly of claim 1 wherein the first transfer element comprises a vacuum roll.

4. The assembly of claim 1 wherein the first selected degree of angular rotation is at least about 25 degrees.

5. The assembly of claim 1 wherein each of the first and second transfer elements comprises a vacuum roll.

6. The assembly of claim 1 wherein the first selected degree of angular rotation is about 40 to about 50 degrees.

7. The assembly of claim 6 wherein the second selected degree of angular rotation is about 40 to about 50 degrees.

8. The assembly of claim 1 wherein the first and second selected degrees of angular rotation are of similar magnitude.

9. The assembly of claim 1 wherein the sum of the first and second degrees of angular rotation is about 90 degrees.

10. An assembly comprising:
    a conveyor including at least a first conveyance surface on which a strip of material is conveyed in a first direction and
    a transfer subassembly including at least a first vacuum transfer roll angularly disposed at a first selected degree of angular rotation relative to the first direction and effective to secure the strip of material from the first conveyance surface and deposit the strip of material on a first adjacent moving surface having a conveyance direction orientated at the first selected degree of angular rotation and a second vacuum transfer roll angularly disposed at a second selected degree of angular rotation relative to the first selected degree of angular rotation and effective to secure the strip of material from the first adjacent moving surface and deposit the strip of material on a second adjacent moving surface having a conveyance direction orientated at the second selected degree of angular rotation,
    wherein the first conveyance surface and the first vacuum transfer roll have conveyance velocities with similar magnitude components in the first direction and wherein the first adjacent moving surface and the second vacuum transfer roll have conveyance velocities with similar magnitude components in the conveyance direction of the first adjacent moving surface.

11. The assembly of claim 10 wherein the first selected degree of angular rotation is 40 to about 50 degrees.

12. The assembly of claim 10 wherein the first selected degree of angular rotation is about 40 to about 50 degrees.

13. The assembly of claim 10 wherein the first and second selected degrees of angular rotation are of similar magnitude.

14. The assembly of claim 10 wherein the sum of the first and second degrees of angular rotation is about 90 degrees.

15. A method for rotating a strip of material and placing the rotated strip of material in surface contact with a moving surface comprising:
    providing at least one strip of material having a first axis in a first angular orientation on a first continuously moving conveyance surface,
    securing the at least one strip of material from the first conveyance surface onto a first transfer element angularly disposed at a first selected degree of angular rotation relative to the first angular orientation,
    transferring the at least one strip of material from the first transfer element onto a first adjacent moving surface,
    securing the at least one strip of material from the first adjacent moving surface onto a second transfer element angularly disposed at a second selected degree of angular rotation relative to the first selected degree of angular orientation and
    transferring the at least one strip of material from the second transfer element onto a second moving surface, wherein at least one of the first and second transfer elements comprises a vacuum roll.

16. The method of claim 15 wherein the first conveyance surface and the first transfer element have conveyance velocities with similar magnitude components in the first direction.

17. The method of claim 15 wherein the first transfer element comprises a vacuum roll.

18. The method of claim 15 wherein the first transfer element is angularly disposed at least about 25 degrees relative to the first angular orientation.

19. The method of claim 18 wherein the first transfer element is angularly disposed about 40 to about 50 degrees relative to the first angular orientation.

20. The method of claim 15 wherein each of the first and second transfer elements comprises a vacuum roll.

21. The method of claim 15 wherein the second transfer element is angularly disposed about 40 to about 50 degrees relative to the first selected degree of angular orientation.

22. The method of claim 15 wherein the first and second transfer elements are each angularly disposed at selected degrees of angular rotation of similar magnitude relative to the first angular orientation and first selected degree of angular orientation, respectively.

23. The method of claim 15 wherein the sum of the first and second degrees of angular rotation is about 90 degrees.

24. An assembly comprising:
a conveyor including at least a first conveyance surface on which a strip of material is conveyed in a first direction and
a transfer subassembly including at least a first transfer element angularly disposed at a first selected degree of angular rotation relative to the first direction and effective to secure the strip of material from the first conveyance surface and deposit the strip of material on a first adjacent moving surface moving at the first selected degree of angular rotation, the transfer subassembly also including a second transfer element angularly disposed at a second selected degree of angular rotation relative to the first selected degree of angular rotation and effective to secure the strip of material from the first adjacent moving surface and deposit the strip of material on a second adjacent moving surface moving at the second selected degree of angular rotation and wherein at least one of the first and second selected degrees of angular rotation is about 40 to about 50 degrees.

25. The assembly of claim 24 wherein the first conveyance surface and the first transfer element have conveyance velocities with same magnitude components in the first direction.

26. The assembly of claim 24 wherein the first transfer element comprises a vacuum roll.

27. The assembly of claim 24 wherein the first selected degree of angular rotation is at least 25 degrees.

28. The assembly of claim 27 wherein the first selected degree of angular rotation is about 40 to about 50 degrees.

29. The assembly of claim 28 wherein at least one of the first and, second transfer elements comprises a vacuum roll.

30. The assembly of claim 29 wherein each of the first and second transfer elements comprises a vacuum roll.

31. The assembly of claim 28 wherein the second selected degree of angular rotation is about 40 to about 50 degrees.

32. The assembly of claim 24 wherein the sum of the first and second degrees of angular rotation is about 90 degrees.

* * * * *